United States Patent [19]
Jacobsen et al.

[11] Patent Number: 6,160,478
[45] Date of Patent: Dec. 12, 2000

[54] WIRELESS HEALTH MONITORING SYSTEM

[75] Inventors: Stephen C Jacobsen; Tomasz J. Petelenz; Stephen C. Peterson, all of Salt Lake City, Utah

[73] Assignee: Sarcos LC, Salt Lake City, Utah

[21] Appl. No.: 09/179,668

[22] Filed: Oct. 27, 1998

[51] Int. Cl.[7] .............................. G08B 1/08; G08B 23/00; A61B 5/00

[52] U.S. Cl. ...................... 340/539; 340/573.1; 340/689; 128/903; 600/300

[58] Field of Search ................................ 340/539, 573.1, 340/825.36, 825.49, 689; 128/903, 904; 600/300

[56] References Cited

U.S. PATENT DOCUMENTS

| | | | |
|---|---|---|---|
| 4,295,133 | 10/1981 | Vance | 340/666 |
| 4,858,622 | 8/1989 | Osterwell | 128/782 |
| 5,012,411 | 4/1991 | Policastro et al. | 128/710 |
| 5,515,858 | 5/1996 | Myllymäki | 128/690 |
| 5,519,380 | 5/1996 | Edwards | 340/539 |
| 5,544,661 | 8/1996 | Davis et al. | 128/700 |
| 5,564,429 | 10/1996 | Bornn et al. | 128/696 |
| 5,722,999 | 3/1998 | Snell | 607/32 |
| 5,752,976 | 5/1998 | Duffin et al. | 607/32 |

*Primary Examiner*—Donnie L. Crosland
*Attorney, Agent, or Firm*—Thorpe, North & Western, LLP

[57] ABSTRACT

A system for remotely monitoring a person's physical activity includes at least one accelerometer capable of measuring both the magnitude and direction of an acceleration. The acceleration data is processed to determine motion/position status and to decide whether there is a likelihood that the person has fallen, and if so, the likely direction that the person has fallen. Based on this data, the likely severity of the fall is calculated. If the severity of the fall is outside an acceptable limit, an alert state is reached upon which a signal is communicated to a remote monitoring unit. Likewise, various physiological conditions may be measured to determine the existence of any anomalous vital signs that would trigger an alarm state. If so, the remote monitoring unit will sound or otherwise communicate an alarm to a person associated with the remote monitoring unit.

43 Claims, 4 Drawing Sheets

WIRELESS HEALTH MONITORING SYSTEM

BACKGROUND

The present invention relates to a system for remote monitoring of individuals, and especially to a system for monitoring the physical activity, body position and occurrence of falls of a person being monitored.

In many situations, hospitalization or constant supervision of persons who are physically handicapped or elderly is not warranted nor feasible. The same may be true when an infirmity related to, for example, illness, injury, or some other medical condition does not warrant staying at a hospital or other medical facility. Such persons may be allowed to return home or to some other remote location away from the hospital or medical facility at which the individual is a patient. Accordingly, many such persons are left unattended without a care giver knowing the state of that individual. Moreover, even in facilities such as a nursing home or other supervised care facility, those responsible to ensure the care of their patients may not know for minutes to hours (or longer) if or when a patient has fallen.

In these circumstances, it may be desirable to monitor the body position of the person at any given time in order to determine whether there is a possibility that the person has fallen. One device known in the art for detecting when a person has fallen is disclosed in U.S. Pat. No. 4,858,622 to Osterweil and includes a harness having a ferromagnetic shunt that is attached to the person being monitored. While the person is lying in bed, the shunt is attached to a sensing means. When the monitored person is about to fall out of the bed, the shunt detaches from the sensing means alerting monitoring personnel. The device has many drawbacks including the fact that the system is not completely mobile with the person being monitored.

A similar device is disclosed in U.S. Pat. No. 5,519,380 to Edwards in which a bed monitoring system detects an attempted departure from a bed or the like by a monitored person. The system generates an RF signal to produce an alarm signal whenever an ankle bracelet or some other device worn by the monitored person moves outside of the monitored volume. Such a device, however, only provides an indication of relative position, not the actual state of the person being monitored.

Likewise, in U.S. Pat. No. 4,295,133, an apparatus for indicating when a patient has evacuated a bed or demonstrates a restless condition is disclosed. In this device, a switch is placed in a bed under the patient which includes two spaced parallel strips of insulating material carrying contact means therebetween. When the strips are straight, the switch is closed, and when the strips are bent into an arc, the switch is open. Closing the switch activates an electrical oscillator, which in turn activates a counter. Upon reaching a selected count, an alarm is activated. Again, however, this device has many drawbacks including its immobility relative to the patient.

U.S. Pat. No. 5,515,858 to Myllymaki discloses a wrist-held monitoring device for independently observing the physical condition of a person by means of motoric activity or movement and physiological conditions, e.g., temperature and/or electric conductivity of the skin. The invention also discloses the use of an acceleration sensor which may be used to indicate the rate of acceleration of the individual's hand movements. This device, however, merely senses the presence or absence of movement of the monitored individual, and in particular, his/her hand/wrist, which is insufficient in determining if a person has fallen.

It is believed that if some or all of the problems associated with the prior art were adequately addressed, more effective monitoring of a patient could be maintained while allowing the patient to be mobile and to conduct an independent lifestyle. In addition, by providing accurate information about the relative movement and position of the individual, a system for monitoring individuals could save many lives. Such a system would be able to automatically monitor the physical activity and body position of a person and, if data generated by the monitoring exceeds predetermined parameters indicative of an alert state, appropriate care givers or those in a monitoring capacity could be directly alerted to the condition.

Thus, there is a need for a monitoring system that may be worn by individuals where monitoring movement and body position of the person may be beneficial to the welfare of the individual. Such a system preferably can independently determine when certain physical conditions may be present and can alert monitoring personnel or a family member that such a condition may exist.

The system may also include a means for transmitting data to a remote location where one or more persons may be monitored simultaneously. Moreover, all of the units may be interconnected via preexisting communications systems, allowing all units to operate and be monitored without the need for relatively expensive independent communications systems.

SUMMARY OF THE INVENTION

It is an object of the present invention to provide a system for monitoring an individual that measures the acceleration of at least one body part of the person.

It is also an object of the present invention to transmit or otherwise communicate the acceleration data, or interpret these data and transmit the result, to a remote location.

It is also an object of the present invention to measure the acceleration in three dimensions and in magnitude such that the direction and severity of the acceleration can be determined.

It is also an object of the present invention to provide an interpretive algorithm to determine whether a person wearing a system has fallen.

It is another object of the present invention to provide such a system for monitoring individuals that is inexpensive and easy to operate.

It is yet another object of the present invention to provide a system for monitoring an individual which is ergonomically designed so it will not interfere or will minimally interfere with the mobility of the individual in the performance of exercise or other tasks.

It is yet another object of the invention to provide a system for monitoring an individual which can be used in both an unsupervised (e.g. home) and a supervised (e.g. hospital, nursing home) environment.

It is still another object of the present invention to provide such a monitoring system which will identify the user in need of attention.

These and other objects not specifically recited are realized in a system for monitoring physical activity of a person in accordance with the principles of the present invention. The system generally comprises sensor means disposed on at least one body part of the person for measuring a magnitude and relative direction of acceleration of movement of the body part and generating a signal indicative of the measured acceleration, a processing means associated with the sensor means for receiving the signal from the sensor means and converting the signal into data, means for interpretation of said data, a first communication means associated with the processor means for sending the data to a remote location, and a second communication means for receiving the data from the first communication means at some remote location.

Preferably, the sensor means comprises at least one accelerometer, such as a multi-dimensional accelerometer capable of measuring acceleration in more than one direction. Alternatively, the sensor means could be comprised of a plurality of accelerometers positioned in different orientations such that an acceleration in any direction can be extrapolated by the accelerations indicated by each of the accelerometers.

In addition, it is preferable that the processing means comprises a microprocessor and further includes software and/or firmware capable of determining whether a fall has occurred, the severity of a fall, and the body position of the person after the fall.

It is also preferable that the communications means comprises a device capable of communicating by local RF, cellular networks, and/or telephone land lines. Likewise, the second communications means is capable of receiving signals by local RF, cellular networks, and/or telephone land lines.

In a preferred embodiment, the processing means is capable of comparing the sensor data with predetermined acceptable ranges and storing the sensor data. The stored data can be transmitted on schedule, upon detection of a predetermined state, or can be retrieved on demand. If the sensor data is outside the acceptable ranges, the system further may include an alarm for generating a humanly perceptible alarm. In a preferred embodiment, the alarm is associated with the second communications means.

In yet another preferred embodiment, the second communications means further includes a display for displaying information indicative of the data such as the severity of the fall and the current position of the person.

It is also contemplated that the second communications means includes a data storage mechanism storing a plurality of acceptable ranges of accelerations and a processor for comparing data received from the first communications means with the acceptable ranges stored in the data storage mechanism. Likewise, the data storage mechanism may include storage means for storing sensor data received from the first communications means.

In yet another preferred embodiment, the system in accordance with the present invention includes at least one physiological sensor for being disposed on the person capable of generating a signal indicative of the physiological condition. The physiological sensor is in communication with the processing device preferably by means of a wireless local area network relative to the body of the user. The physiological sensor may comprise a pulse sensor, a blood pressure sensor, and/or an ECG sensor.

The present invention also includes a method of monitoring the physical activity of a person in which the method includes measuring the relative movement of the person, generating signals representing the measured movement, transmitting the signals to a base unit, processing the signals into data, and comparing the data with acceptable ranges, or states. The method is preferably accomplished by securing at least one sensor to the person and communication data generated by the sensor by employing a satellite, radio waves, and/or a land line. Such systems may include call pagers, telephones, land lines, and the like.

The method may also include the steps of measuring at least one physiological parameter, generating a signal indicative thereof, comparing the signal with at least one value indicative of a limit of the physiological parameter, and determining whether the physiological parameter is within the limit. The method may also include the means to determine fall state using multi-parameter input data, and means of comparing current data to the predetermined state information.

The present invention is capable of determining whether a monitored individual is walking, running, or staying relatively still, whether the person has fallen, and whether the person is currently prone, supine or vertical. Moreover, the system in accordance with the present invention is capable of sensing the direction that the person has fallen. The system is also capable of measuring various physiological parameters of the person. If an alarm state is reached in that it is determined that a fall has likely occurred or that a physiological parameter has been exceeded, a humanly perceptible alarm is generated indicating that measured physical and/or physiological conditions are outside of the acceptable ranges/states.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Figure 1:
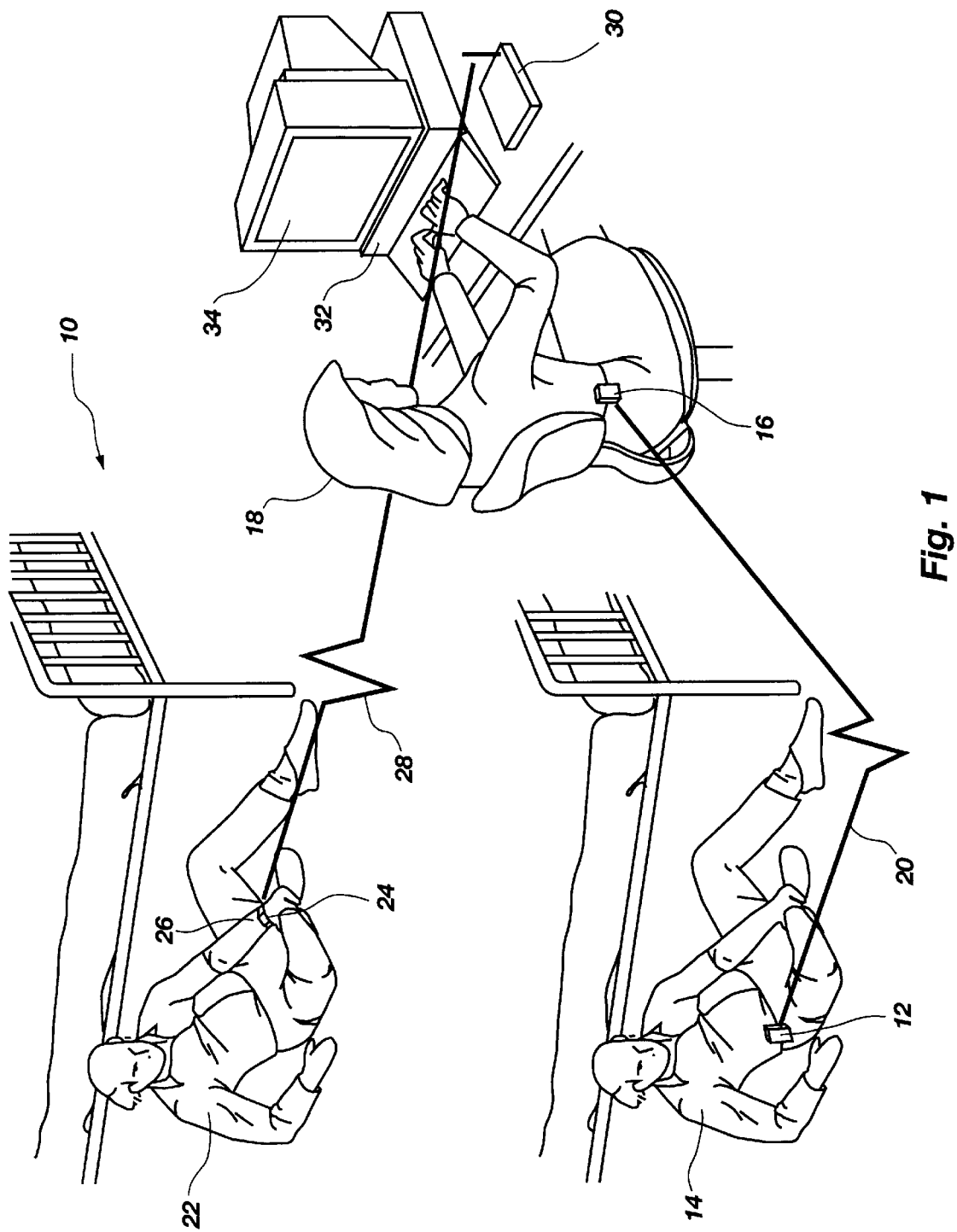
FIG. 1 is a schematic representation of a first preferred embodiment of a personal monitoring system in accordance with the present invention in which more than one person can be monitored by a single individual.

Reference will now be made to the drawings in which the various elements of the present invention will be given numerical designations and in which the invention will be discussed so as to enable one skilled in the art to make and use the invention. As illustrated in FIG. 1, the wireless health monitoring system, generally indicated at 10, comprises a monitoring unit 12 configured for wearing by an individual 14 to be monitored particularly configured for detecting a fall. The monitoring unit 12 is in communication with a remote unit 16 configured to be worn by a person 18 responsible for monitoring the well-being of the individual 14. The means of communication between the monitoring unit 12 and the remote unit 16, indicated by line 20, may include radio frequency (RF) transmissions, cellular communications networks (e.g., both digital and analog, similar to those used in current pager technologies), telephone land lines, or other means of communication known in the art.

As further illustrated in FIG. 1, the person 18 responsible for monitoring may monitor more than one individual simultaneously using similar or different means of communication. For example, the additional individual 22 is provided with a monitoring unit 24 configured for wearing on a wrist 26 and is in communication, represented by line 28 with a remote base unit 30 configured for receiving the signal 28 from the monitoring unit 24. It should be noted that while the person 18 responsible for monitoring the individuals 14 and 22 is illustrated as utilizing two different remote units 16 and 30, it is contemplated as will be described in more detail that a single remote unit 16 or 30 could be employed to monitor multiple monitoring units 12 and 24. Upon receiving an alert signal 20 or 28, the person 18 responsible for monitoring could input into a computer 32 information such as the person from whom the alert signal 20 or 28 was received, the time of receipt of the alert signal 20 or 28, and could quickly alert another individual to respond to the alert signal 20 or 28 by checking on the particular individual 14 or 22 from whom the alert signal 20 or 28 was received. Moreover, the system 10 may be configured to automatically display information as on a computer display 34 such as the person 14 or 22 from whom the alert signal 20 or 28 was received, their location, the time the alert signal 20 or 28 was received, and the believed severity of the fall that triggered the alert signal 20 and 28. Likewise, some or all of this information could be displayed on the pager-like remote unit 16 such that the person 18 responsible for monitoring could be at any location and receive information necessary to determine the person from whom the alert signal was received.

Figure 2:
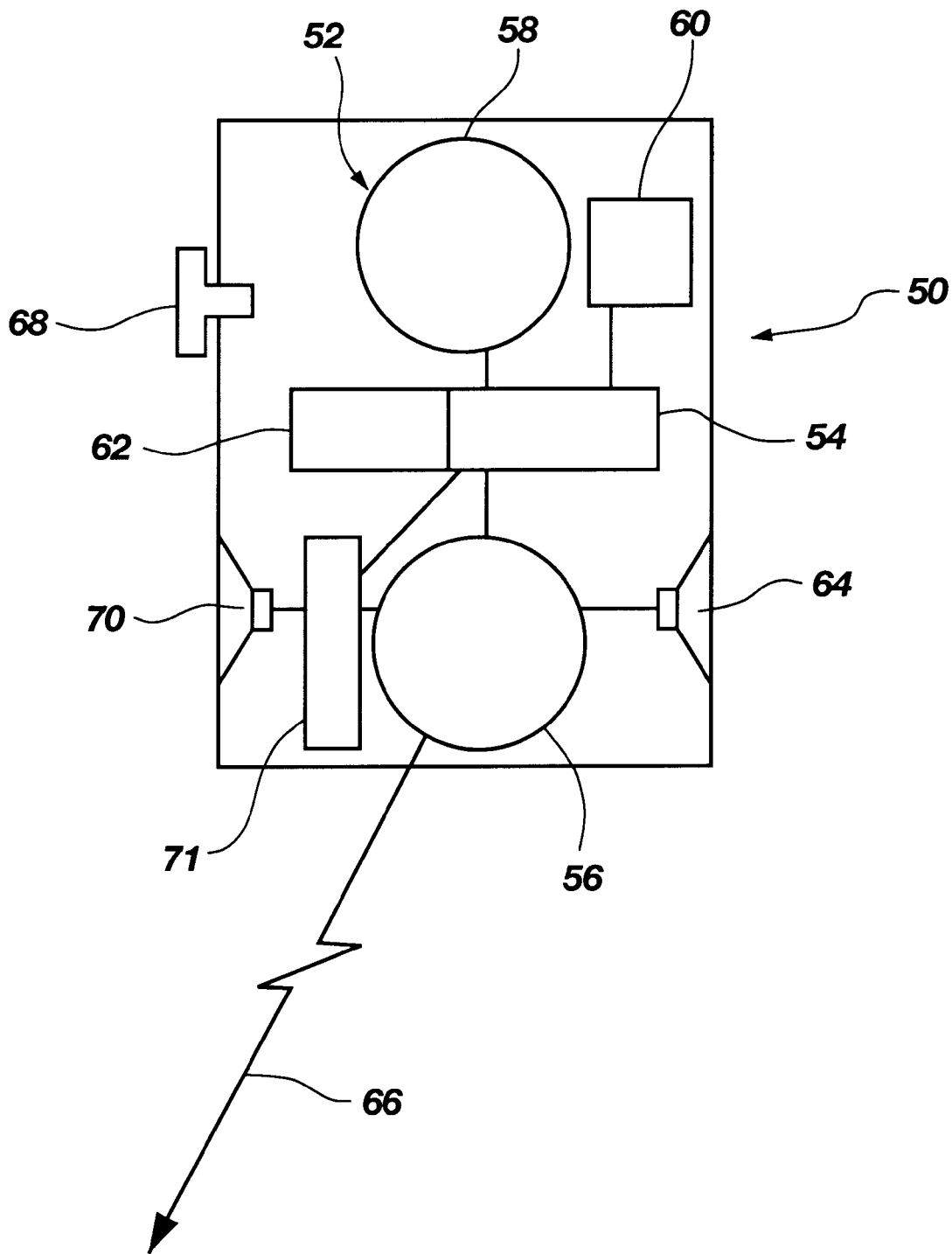
FIG. 2 is a schematic view of a preferred embodiment of a monitoring unit in accordance with the present invention.

Referring now to FIG. 2, a monitoring unit, generally indicated at 50 comprises a physical activity sensor 52, a processor 54, and a communications device 56. The sensor 52 preferably comprises at least one accelerometer 58 capable of sensing or detecting movement or acceleration in three dimensions. That is in an x, y, z coordinate system, the accelerometer 58 can detect an acceleration in both positive and negative x-direction, positive and negative y-direction, and positive and negative z-direction. Thus, an acceleration which occurs in a direction that is not purely in the x, y, or z-direction (i.e., a direction that is a combination of x and y, y and z, or z and x) can be determined by vector analysis to determine the actual direction of the acceleration. As further illustrated in FIG. 2, the sensor 52 further includes a position sensor 60 that can detect the position of the person wearing the monitoring unit 50. For example, the position sensor may detect whether the person is prone, supine, vertical, on a side, any position thereinbetween, and combinations thereof.

Signals generated by the sensor 52 are received by the processing unit 54. The processing unit 54 preferably comprises a microprocessor and associated firmware and software to interpret the signals received from the sensor 52. Likewise, the processing unit 54 may be comprised of analog circuitry capable of sensing when an event has occurred and triggering an alert state. The signals received from the sensor 52 are interpreted by the processor 54 to determine the possible severity of a fall (such as the degree of the impact, the direction of the fall, velocity of the fall, etc.), motion, and/or body position.

This interpretation is preferably performed by employing a body position/motion/fall event algorithm. For example, when a person is running or walking, the accelerometer 58 should provide a rhythmic pattern of pulses, the magnitude and frequency of which are dependent upon the level (i.e., the speed and intensity) of the exercise. Moreover, abrupt accelerations resulting from abrupt changes in direction, jumping actions, and the like may produce an accelerometer output signal (a "spike" pulse) that would otherwise signal that a fall event has occurred. However, the processor 54 will determine whether such a spike pulse is likely the result of a jump or whether it has been likely caused by a fall depending on other sensor information. This other sensor information may include sensor data from the sensor 60 as well as sensor data that was received from both the sensor 58 and the sensor 60 prior to the spike pulse and sensor data that has been received from the sensors 58 and 60 since the spike pulse. For example, if the sensor 52 detects a spike pulse of a value sufficient to indicate that the person being monitored may have fallen, the processor 54 will evaluate other data that it has received in order to determine whether an actual fall is likely. The evaluation may merely entail determining the position in which the person is likely to be based upon data received from the position sensor 60. Preferably, however, the processor 54 also includes a data storage mechanism 62 in which readings taken from the sensors 58 and 60 are recorded for a period of time (e.g., continuous, ten seconds, one minute, five minutes, etc.). Thus, upon receiving a spike pulse of sufficient intensity, the processor 54 may access its memory or data storage device 62 to determine the state the person was in prior to the change in accelerometer output. Likewise, the processor may continue to receive sensor data from the sensors 58 and 60 for some period of time (e.g., 10 seconds, one minute, etc.) to evaluate the state of the person being monitored after the spike pulse.

If, for example, sensor data from sensor 60 indicates that a person was in a prone or supine position and sensor 58 senses little or no movement prior to a spike pulse, it is likely that the person has fallen from a bed or sofa and should be contacted either in person or by telephone to ensure that the person has not been injured. In another example, if the sensor data from sensor 60 indicates that the person was in a vertical position and sensor 58 sensed walking movement prior to a spike pulse, sensor data from sensors 58 and 60 after the spike pulse may provide information to adequately determine whether or not the person has fallen and the severity of such a fall. For example, if the sensor 60 indicates that the person is in a prone position following a spike pulse and remains there for any length of time, the processor 54 may determine that a fall has occurred and that the fall is likely a serious fall. The severity of such a fall may also be determined by the magnitude of the spike pulse. Likewise, if the sensor 60 indicates that the person is in a prone position immediately following a spike pulse, but quickly returns to a vertical position, the processor 54 may determine that a fall has occurred, but that the fall is not likely to be a severe fall.

It is also preferable that the sensor 58 be comprised of a three dimensional accelerometer, that is, that accelerations in all directions can be sensed. Thus, in the situation when the processor 54 determines that a fall has likely occurred, the severity of the fall may also be likely increased if the fall occurred backwards or to the side. In any event, once the processor 54 has determined that a fall has likely occurred, the communications device 56 transmits an alert signal to a remote unit (not shown). In addition, it may be preferable to provide a speaker 64 from which a beep or other alarm may sound to warn the person being monitored that the processor 54 has detected a fall event. If indeed the person has fallen and is in need of assistance, the person need not do anything as an alarm signal, indicated by line 66, will automatically be transmitted. If, however, the processor has incorrectly sensed a fall, as may be the case if the person accidentally drops the monitoring unit 50 when removing it or if the person wearing the monitoring unit 50 causes the monitoring unit 50 to impact a stationary object, the person may disable or stop the alert signal 66 from being transmitted by pressing a button 68. Preferably, the button 68 must be pressed before the beep from the speaker 64 stops sounding (e.g., five seconds, ten seconds, etc.).

The method of detecting falls, described above, is only an example of one possible algorithmic approach to determining whether a fall event has occurred. Other algorithms using Artificial Intelligence or Fuzzy Logic methods may be employed as well, and are anticipated by this invention.

Assuming that the alert signal 66 is transmitted to a person responsible for monitoring such alert signals 66, such as a care giver, nurse or other health care professional, it is also preferable that the monitoring unit 50 provide a two-way communications device. Thus, the monitoring unit 50 is provided with a microphone 70 through which the person being monitored can verbally indicate whether or not they have received any injuries. In addition, the speaker 64 may be employed to provide voice communication from the person responsible for monitoring. Such two-way communication may be important especially in situations where the monitored person has fallen and cannot get to a telephone.

As will be described in more detail, the monitoring unit 50 also includes a local area communications device 71, such as an RF signal receiver, that can receive RF signals from various other physiological sensors that may be disposed on the person being monitored. For example, such vital signs as heart rate, blood pressure, and other physiological conditions can be monitored through a plurality of sensors that transmit their readings in the form of wireless communication to the receiver 71. The receiver 71 can then relay this information to the processing device 54 for a determination of whether the vital sign(s) are within normal parameters. For example, cardiac arrhythmias that can be correlated with the fall event may indicate a possible cause of the fall. If not, an alert signal 66, as previously discussed, may be transmitted.

Figure 3:
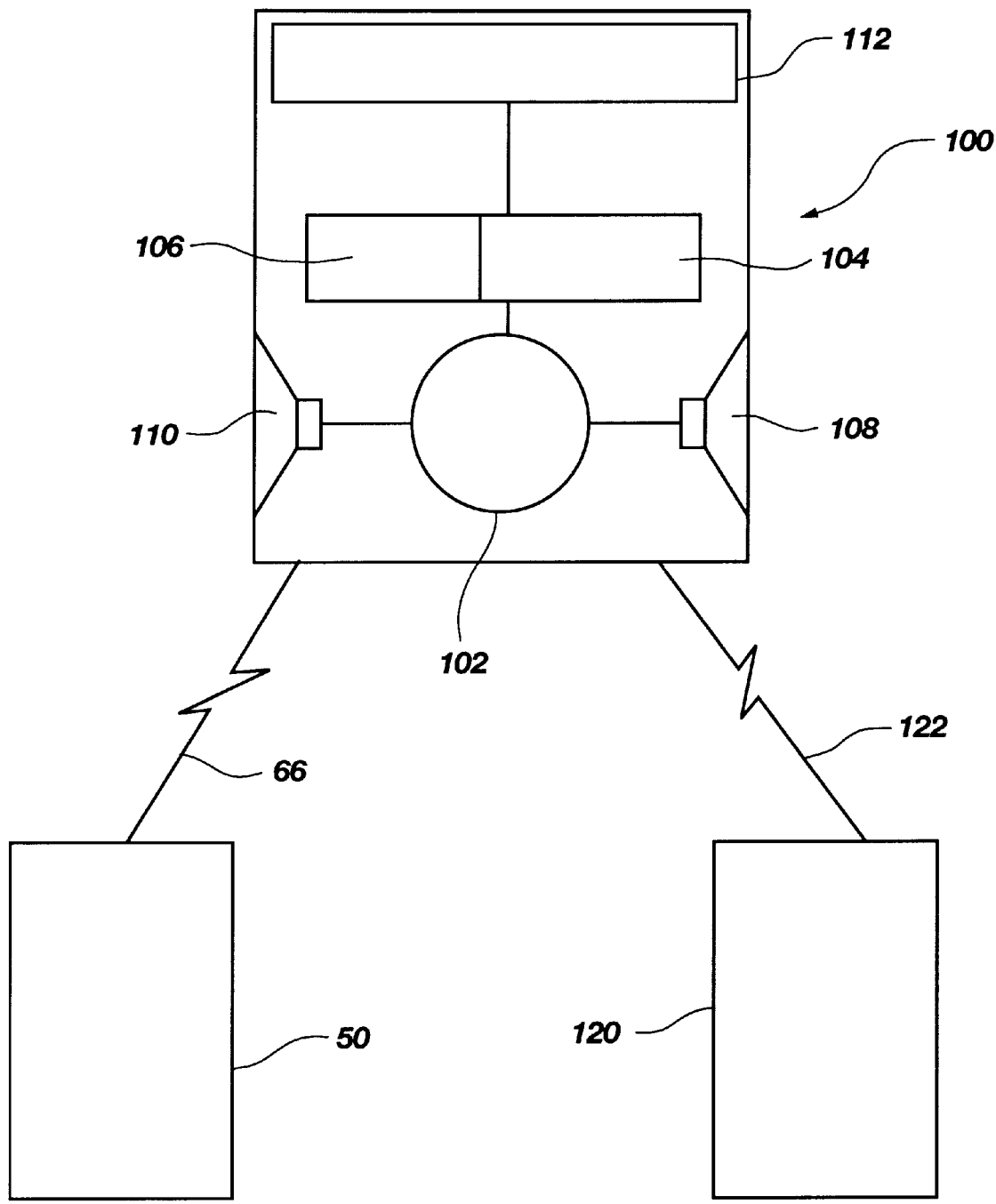
FIG. 3 is a schematic view of a preferred embodiment of a remote unit in accordance with the present invention.

Referring now to FIG. 3, the monitoring unit, generally indicated at 100, comprises a communications device 102 for receiving a signal 66 from a monitoring unit 50 (see FIG. 2). The monitoring unit 100 also preferably includes a processor 104, a memory mechanism or data storage device 106, a speaker 108, a microphone 110, and a display 112. As such, the monitoring unit 100 can act in a passive capacity while waiting for an alert signal to be transmitted by the monitoring unit 50. Conversely, after receiving such an alert signal 66, the monitoring unit can become a more proactive device as it displays information relevant to the alert signal 66 on the display 112 as well as having the capability to provide two way communication with the relevant monitoring unit 50 by utilizing its speaker 108 and microphone 110.

Preferably, the remote unit 100 is capable of monitoring more than one monitoring unit, such as monitoring units 50 and 120. Accordingly, the alert signal 66 and 122, respectively, initially transmits more than just a simple alert signal. For example, the remote unit 100 and monitoring units 50 and 120 may employ existing cellular networks for communications purposes. As such, each of the units 100, 50 and 120 may act in a similar manner to cellular telephones. That is, when an alert condition is realized by a monitoring unit 50, the monitoring unit 50 would essentially call the monitoring unit 100 through cellular communications networks. As such, similar to the existence of unique telephone numbers, the remote unit would be programmed with a unique identification code and would transmit that code to the monitoring unit 100. The monitoring unit 100 would recognize the source of the alert signal 66 similar to a cellular phone having "caller ID" in which, for example, the name of the individual from whom the alert signal 66 was received would be displayed on the display 112. As such, the monitoring unit 100 can monitor multiple monitoring units 50 and 120 and be able to identify the source of an alert signal 66 or 122.

Additionally, because the remote units 50 and 120 and the monitoring unit 100 may use existing cellular telephone networks, audio communication between the relevant remote unit and the monitoring unit 100 can occur. That is, once the "call" is made by the monitoring unit 50, a communications link is created through which data can be transmitted. This data may include the specifics of the fall that caused the alert signal 66 to be sent, such as the severity, direction, and present position of the patient. Moreover, this data may comprise two way communication between the person wearing the monitoring unit 50 and the person monitoring the remote unit 100. As such, the person monitoring the remote unit 100 can ask the person wearing the monitoring unit if assistance is necessary. The use of such communications systems can provide for communications relay in a vehicle, such as a car or bus, allowing a person to gain greater mobility and independence and thus improving one's quality of life.

It is also contemplated that the remote unit 100 and the monitoring units 50 and 120 be configured with more local communications means such as by employing an RF signal. Such a system may be desirable in hospital and nursing home settings where it is not necessary for alert signals 66 and 122 to travel long distances, as may be the case where an elderly person is being monitored in his or her home by a family member or care giver that may be several miles away. In such a hospital or nursing home setting, the monitoring units may simply send a signal when an acceleration abruptly changes and/or exceeds some predetermined threshold. Referring again to FIG. 2, in such a situation, the data storage device may contain data that indicates maximum allowable acceleration changes or absolute maximum acceleration values, above which would result in an alert signal 66 being sent by the communications device 56. Such changes in acceleration would preferably be at different times with time constants set to provide a maximum allowable acceleration change. Thus, the relative state of the person may be measured at various or regular time intervals. When the processor 54 receives data from the acceleration device 58 that is greater than a relevant value retrieved from the data storage device 62, or has substantially changed from a previous reading to indicate an anomalous condition, the alert signal 66 containing an identification code is immediately sent. The monitoring unit 100, which may be a pager-like device or a base unit located at a nurse's station, will immediately provide an alarm, such as a series of beeps, tones, or the like and will display information to allow the care giver to locate the particular individual from whom the alert signal 66 was sent. Thus, in such situations, the monitoring unit 50 may not require two-way communications or the ability to more precisely determine if a fall has actually occurred.

Figure 4:
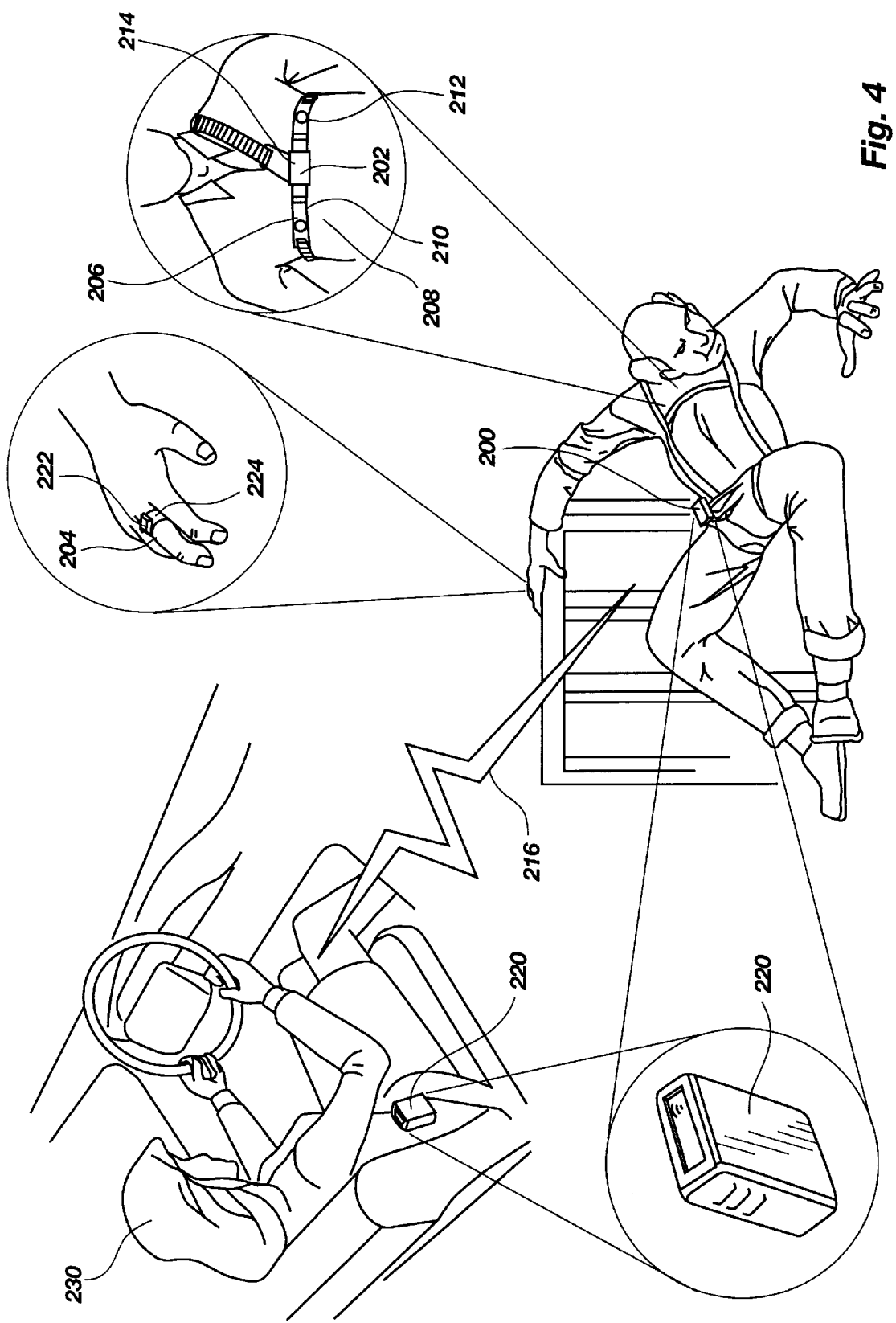
FIG. 4 is a schematic representation of a second preferred embodiment of a personal monitoring system in accordance with the present invention in which various vital signs of the person being monitored are automatically taken.

As further illustrated in FIG. 4, a monitoring unit 200 may be incorporated with other sensor units 202 and 204 which may provide physiological data that may also be monitored. As shown, a band or strap 206 is configured to be placed around the chest 208 of the user and is provided with a plurality of ECG sensors 210 and 212. A local area communications device 214 transmits the ECG data received from the ECG sensors 210 and 212 to the monitoring unit 200. If the monitoring unit detects an anomalous ECG reading, which may indicate, for example, a cardiac arrhythmia, an alert signal 216 will be sent to a monitoring unit 220.

Similarly, the sensor unit 204, which may be worn on the finger of the user, is configured with one or more sensors 222 such as a pulse sensor and/or blood pressure sensor. The sensor unit 204 also includes a communications device 224 which may communicate by local RF to the monitoring unit 200. An anomalous reading by the sensor unit 204 detected by the monitoring unit 200 will result in an alert signal 216 being sent to the remote unit 220 alerting the person 230 responsible for monitoring. It is also contemplated that such sensors may detect such physiological conditions as $S_pO_2$ levels and blood perfusion.

Accordingly, the system of the present invention could present significant cost savings for health care providers. For example, rather than requiring nurses to constantly check on patients that are prone to falling, such events can be automatically monitored. Moreover, those who are concerned about relatives who commonly fall can be put at ease knowing that any such falls are being monitored. In addition, the system provides means for health care providers to monitor vital signs without having to be at the patients bedside. Thus, a smaller number of nurses could be used while providing a higher level of care.

Thus, there is disclosed a system for remotely monitoring the activity of a person and for detecting the possibility of a fall. In addition, the system is capable of monitoring vital signs. Upon detecting a fall or an abnormal vital sign(s), the system is capable of alerting a care giver of such an event. Those skilled in the art, however, will recognize that numerous modifications, including combinations of the illustrated embodiments, can be made without departing from the scope or spirit of the present invention. The appended claims are intended to cover such modifications and combinations.

What is claimed is:

1. A system for monitoring physical activity of a person, comprising:
    a multi-dimensional accelerometer disposed on at least one body part of the person for measuring a magnitude and relative direction of movement of the body and generating a signal indicative of the measured acceleration;
    processing means associated with the multi-dimensional accelerometer for receiving the signal from the multi-dimensional accelerometer and converting the signal into data, wherein the processing means analyzes data from the multi-dimensional accelerometer until it receives a spike pulse to indicate a possibility that a fall has occurred and then the severity of the fall is determined based on the spike pulse magnitude;
    first communication means associated with the processor means for sending the data to a remote location; and
    second communication means at a remote location for receiving the data from the first communication means.

2. The system of claim 1 wherein the processing means includes a maximum allowable acceleration change value which is compared to the spike pulse, and an alert signal is sent when the spike pulse exceeds the maximum allowable acceleration change value.

3. The system of claim 1 wherein the processing means includes determining whether a person is in a prone position following a spike pulse and sending an alert signal if they remain in a prone position for a selected length of time after a spike pulse.

4. The system of claim 1 wherein the processing means includes determining whether a person is in a prone position following a spike pulse and sending no alert signal if they quickly return to a vertical position within a selected length of time after a spike pulse.

5. The system of claim 1, further comprising at least one physiological sensor disposed on the person for generating a signal indicative of at least one physiological condition and in communication with said processing means.

6. The system of claim 5, further including a wireless local area communications means for communicating between the at least one physiological sensor and said processing means.

7. The system of claim 5, wherein said at least one physiological sensor comprises at least one of a pulse sensor, a blood pressure sensor, an ECG sensor, a $S_pO_2$ sensor, and a blood perfusion sensor.

8. The system of claim 1, wherein said first communications means comprises a device capable of communicating by at least one of: local RF, cellular networks, and telephone land lines.

9. The system of claim 1, wherein said second communications means comprises a device capable of communicating with said first communications means by at least one of: local RF, cellular networks, and telephone land lines.

10. The system of claim 1, wherein said processing means includes means for comparing the data with predetermined acceptable ranges.

11. The system of claim 10, wherein said processing means further includes data storage means for recording said sensor data.

12. The system of claim 11, wherein said processor means further comprises access means for enabling access to information recorded in the data storage means.

13. The system of claim 10, further comprising alarm means for generating a humanly perceptible alarm when the data is outside a predetermined range.

14. The system of claim 13, wherein said alarm means is associated with said second communications means.

15. The system of claim 1, wherein said second communications means further includes display means for displaying information based on the data.

16. The system of claim 1, wherein said second communications means further comprises a data storage mechanism having a plurality of acceptable ranges for physiological values stored therein, and processor means for comparing the data received from the first communications means with the acceptable ranges stored in the data storage mechanism.

17. The system of claim 16, wherein the data storage mechanism further comprises storage means for storing sensor data received from the first communications means.

18. A personal alert system for monitoring a person, comprising:
    a monitoring unit configured for wearing by a person and having at least one acceleration sensor disposed thereon for generating sensor data indicative of the magnitude and direction of movement of at least one body part of the person;
    a communications device associated with said at least one acceleration sensor and configured for wearing by the person, said communications device capable of sending a signal to a remote location;
    a processing device, capable of receiving said sensor data, for determining when a spike pulse has been received that indicates the possibility a fall has occurred and then evaluates the severity of the fall based on the spike pulse magnitude; and
    a remote unit for communicating with the communications device and generating an alarm when said processing device causes said alert state.

19. The system of claim 18, wherein said at least one acceleration sensor comprises a multi-dimensional accelerometer.

20. The system of claim 18, wherein said monitoring unit and said communications device are contained within a single relatively small housing configured for wearing by a person.

21. The system of claim 18, wherein said communications device is capable of communicating by at least one of: local RF, cellular networks, and telephone land lines.

22. The system of claim 21, wherein said remote unit is capable of communicating with said communications device by at least one of: local RF, cellular networks, and telephone land lines.

23. The system of claim 22, wherein said remote unit comprises a pager.

24. The system of claim 18, wherein said processing device includes at least one of firmware and software for comparing the data with predetermined acceptable ranges.

25. The system of claim 24, wherein said processing device further includes data storage means for recording said sensor data and storing said predetermined acceptable ranges.

26. The system of claim 25, further including access means associated with said processing device for enabling access to information recorded in the data storage means.

27. The system of claim 24, further comprising a humanly perceptible alarm associated with said remote unit for providing an alarm when the data is outside a predetermined range.

28. The system of claim 27, wherein said remote unit further includes display means for displaying information based upon the data.

29. The apparatus of claim 18, wherein said remote unit further comprises a data storage mechanism having a plurality of acceptable ranges for physiological values stored therein, and processor means for comparing the data received from the first communications means with the acceptable ranges stored in the data storage mechanism.

30. The apparatus of claim 29, wherein the data storage mechanism is capable of storing sensor data received from the communications device.

31. The system of claim 18, further comprising at least one physiological sensor disposed on the person for generating a signal indicative of at least one physiological condition in communication with said processing device.

32. The system of claim 31, further including a wireless local area network for communicating between the at least one physiological sensor and said processing device.

33. The system of claim 31, wherein said at least one physiological sensor comprises at least one of a pulse sensor, a blood pressure sensor, an ECG sensor, a $S_pO_2$ sensor, and a blood perfusion sensor.

34. A method of monitoring physical activity of a person, comprising:

measuring relative movement of the person with a multi-dimensional accelerometer;

generating signals representing the measured movement;

transmitting the signals to a base unit;

processing the signals into data; and comparing the data until a spike pulse is received from the multi-dimensional accelerometer to indicate the possibility that a fall has occurred and then the severity of the fall is determined based on spike pulse magnitude.

35. The method of claim 34, wherein said measuring includes securing at least one sensor to the person.

36. The method of claim 34, wherein the transmitting includes communicating by employing at least one of a satellite, radio waves, and a land line.

37. The method of claim 34, wherein said measuring includes sensing at least one activity selected from the group comprising: walking, running, being still, and falling.

38. The method of claim 37, wherein said measuring includes sensing at least one position of the person selected from the group comprising: prone, supine, vertical, and combinations thereof.

39. The method of claim 38, wherein said sensing the activity of falling further includes sensing the direction that the person has fallen.

40. The method of claim 34, further comprising generating a humanly perceptible signal when the values indicative of the measured physical conditions are outside of the acceptable ranges.

41. The method of claim 34, further including measuring at least one physiological parameter and generating a signal indicative thereof, comparing the signal with at least one value indicative of a limit of said at least one physiological parameter, and determining whether said at least one physiological parameter is beyond said limit.

42. The method of claim 39, further including determining whether a change in other sensor data correlates with the fall.

43. The method of claim 39, further including determining whether a cardiac arrhythmia may have occurred, and correlating such an event with the fall.

\* \* \* \* \*